United States Patent [19]

Hibino et al.

[11] Patent Number: 5,426,018
[45] Date of Patent: Jun. 20, 1995

[54] PHOTOCHROMIC MATERIAL

[75] Inventors: Junichi Hibino; Kumiko Moriyama; Yoshio Kishimoto, all of Hirakata, Japan

[73] Assignee: Matsushita Electric Industrial Co., Ltd., Osaka, Japan

[21] Appl. No.: 152,952

[22] Filed: Nov. 15, 1993

Related U.S. Application Data

[63] Continuation of Ser. No. 842,909, Feb. 27, 1992, abandoned.

[30] Foreign Application Priority Data

Mar. 4, 1991 [JP] Japan ................. 3-063969

[51] Int. Cl.$^6$ ............................................. G03C 1/685
[52] U.S. Cl. ....................... 430/345; 430/945; 430/962; 252/586; 548/409
[58] Field of Search ............ 430/345, 945, 962; 252/586, 587, 589; 548/409

[56] References Cited

U.S. PATENT DOCUMENTS

| | | | |
|---|---|---|---|
| 4,737,427 | 4/1988 | Miyazaki et al. | 430/19 |
| 4,753,867 | 6/1988 | Arakawa et al. | 430/345 |
| 4,794,068 | 12/1988 | Miyazaki et al. | 430/345 |

FOREIGN PATENT DOCUMENTS

| | | | |
|---|---|---|---|
| 0389813 | 10/1990 | European Pat. Off. | 548/409 |
| 0411884 | 2/1991 | European Pat. Off. | 548/409 |
| 61-203450 | 9/1986 | Japan . | |
| 62-165653 | 7/1987 | Japan | 430/270 |
| 63-207887 | 8/1988 | Japan . | |
| 1-259353 | 10/1989 | Japan | 430/345 |
| 1-259357 | 10/1989 | Japan | 252/586 |

OTHER PUBLICATIONS

"Aggregation Control of Photochromic Spiropyrans in Langmuir–Blodgett Films", Proc. 5th Int. Con. on LB Films, Hibino et al, GP 19 (1991).

Hibino et al., Nippon Kagaku Kaishi, No. 10, pp. 1129–1135, Oct. 1990.
Ando et al., "J. Aggregation of Photochrmic Spiropyrans in Langmuir–Blodgett Films", Thin Solid Films, 133, pp. 21–28 (1985).
Seki et al., J. Phys. Chem., 94, pp. 3769–3775, (1990).
Chemical Abstracts, vol. 114, No. 6, Abstract No. 52789F, (Feb. 1991).

*Primary Examiner*—Charles L. Bowers, Jr.
*Assistant Examiner*—John A. McPherson
*Attorney, Agent, or Firm*—Panitch Schwarze Jacobs & Nadel

[57] ABSTRACT

The present invention provides a novel photochromic material which is capable of forming two kinds of aggregates, each having a sharp absorption peak at a different wavelength. The photochromic material comprises a spiropyran compound represented by the following general formula:

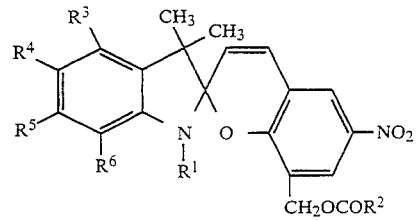

wherein $R^1$ and $R^2$ are independently alkyl groups each containing 1 to 30 carbon atoms, and $R^3$, $R^4$, $R^5$, and $R^6$ are independently selected from the group consisting of hydrogen, an amino group, an alkoxy group with 1 to 5 carbon atoms, and an alkylamino group with 1 to 5 carbon atoms with the proviso that at least one of $R^3$, $R^4$, $R^5$, and $R^6$ is an amino group, an alkoxy group or an alkylamino group.

4 Claims, 2 Drawing Sheets

PHOTOCHROMIC MATERIAL

This application is a continuation of Ser. No. 842,909, filed Feb. 27, 1992, now abandoned.

BACKGROUND OF THE INVENTION

1. Field of the Invention

The present invention relates to a photochromic material and an optical storage medium using the same.

2. Description of the Prior Art

Substances which display reversible color changes upon exposure to light are collectively known as photochromic materials. Spiropyran compounds constitute one of the most intensively studied types of photochromic material.

Many spiropyran compounds have already been reported in the literature. For example, the colorless spiropyran compound A of the following formula is transformed into the red compound merocyanine B by irradiation with ultraviolet rays with a wavelength of approximately 340 nm. The compound B reverts to the form A if irradiated with visible light with a wavelength of approximately 580 nm.

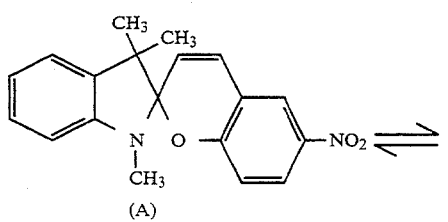

(A)

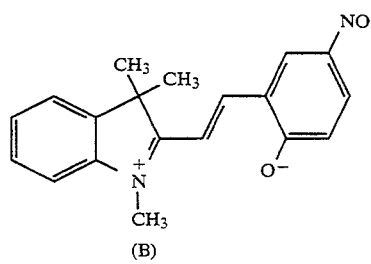

(B)

Optical storage media can be prepared by utilizing these photochromic materials which change their structures by irradiation. For example, the photochromic materials are coated onto a disk to prepare a storage medium, and this storage medium is colored by irradiation with ultraviolet rays, whereby the entire surface is initialized. This medium is irradiated with a laser beam having a wavelength appropriate for changing a colored form to a colorless form, whereby the irradiated portion is recorded. The recorded portion can be initialized by irradiation with ultraviolet rays.

Furthermore, a multifrequency optical recording system taking advantage of the above-mentioned characteristics is proposed in Japanese Laid-Open Patent Publication No. 61-203450. In this system, photochromic materials each having a different absorption sensitivity are laminated to prepare a storage medium, and a laser beam having a wavelength corresponding to each layer is irradiated to the storage medium, whereby each layer is recorded independently. By using this optical recording system, a plurality of informations can be recorded on one spot in high density.

In order to perform this multifrequency optical recording by using photochromic materials, the following conditions 1 and 2 are required:

(1) A colored form should be stable so as to stabilize the initial state, and (2) An absorption peak of photochromic materials should be sharp so as to perform multiple recording effectively.

For satisfying these two conditions, for example, a method for forming an aggregate of a colored form of spiropyran is proposed (Proc. Int. Symp. Future Electron Devices, p47 (1985)).

For example, a spiropyran compound having the following structure C is converted to a colored form D by irradiation of ultraviolet rays, and the colored form D forms an aggregate which is one of these types of molecular assemblies when heated at a temperature of about 35° C. The stability of the aggregate thus obtained is remarkably improved compared with that of its monomer (i.e., the colored form which does not form the aggregate). The absorption maximum of the spectrum moves to a longer wavelength region, and the absorption peak becomes sharp (Thin Solid Films, 133,21(1985)).

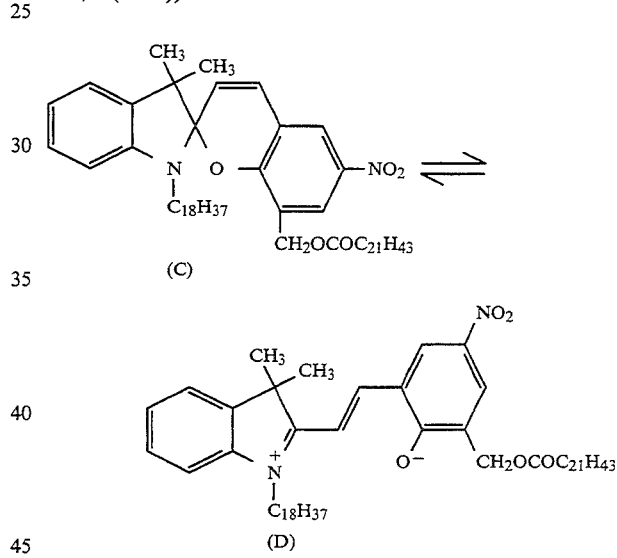

(C)

(D)

A spiropyran compound having the following structure E is converted to a colored form F by irradiation with ultraviolet rays, and the colored form F forms an aggregate which is one of these types of molecular assemblies when heated at a temperature of about 35° C. The stability of the aggregate thus obtained is remarkably improved compared with that of its monomer (i.e., colored form which does not form the aggregate). The absorption maximum of the spectrum moves to a shorter wavelength region, and the absorption peak becomes sharp (J. Phys. Chem., 94,3769(1990)).

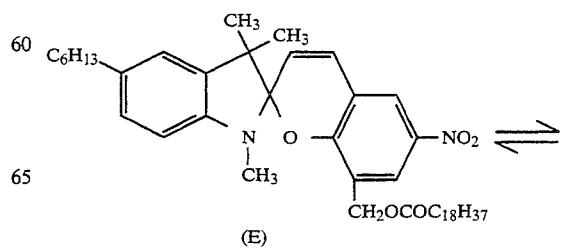

(E)

-continued

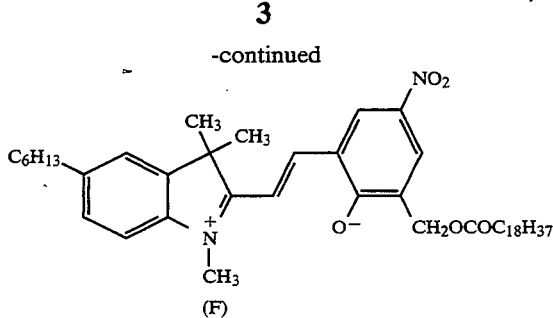

(F)

The aggregate obtained by heating the compound D at a temperature of about 35° C. is considered as an aggregate in which molecules of the compound D gather in a head-to-tail structure. This kind of aggregate is called a J aggregate. The aggregate obtained by heating the compound F at a temperature of about 35° C. is considered as an aggregate in which molecules of the compound F gather in a side-by-side structure. This kind of aggregate is called an H aggregate. As described above, the J aggregate is characterized in that its absorption peak moves to a longer wavelength region compared with that of its monomer, its absorption peak becomes sharp, and it is stabilized. The H aggregate is characterized in that its absorption peak moves to a shorter wavelength region compared with that of its monomer, its absorption peak becomes sharp, and it is stabilized. Thus, it is considered that a multifrequency optical storage medium can be prepared by the use of the J aggregate and the H aggregate in combination.

However, thus far, an H aggregate cannot be formed from a photochromic material which can form a J aggregate, while a J aggregate cannot be formed from a photochromic material which can form an H aggregate. Therefore, in order to prepare such a multifrequency optical storage medium, a plurality of photochromic materials, each of them having different maximum absorption wavelength, are required.

SUMMARY OF THE INVENTION

The present invention, which overcomes the above-discussed and numerous other disadvantages and deficiencies of the prior art, provides a photochromic material comprising a spiropyran compound of formula I:

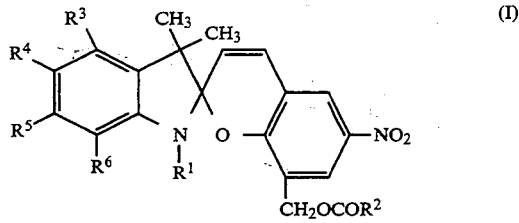

wherein $R^1$ and $R^2$ are independently alkyl groups each containing 1 to 30 carbon atoms, and $R^3$, $R^4$, $R^5$, and $R^6$ are independently selected from the group consisting of hydrogen, an amino group, an alkoxy group with 1 to 5 carbon atoms, and an alkylamino group with 1 to 5 carbon atoms with the proviso that at least one of $R^3$, $R^4$, $R^5$, and $R^6$ is an amino group, an alkoxy group or an alkylamino group.

In a preferred embodiment, at least one of $R^4$ and $R^6$ in formula I is selected from the group consisting of an amino group, an alkoxy group containing 1 to 5 carbon atoms, and an alkylamino group containing 1 to 5 carbon atoms.

In a preferred embodiment, at least one of $R^4$ and $R^6$ in formula I is a methoxy group.

In a preferred embodiment, in formula I, $R^1$ is an octadecyl group, $R^2$ is a heneicosyl group, $R^3$, $R^5$ and $R^6$ are hydrogen, and $R^4$ is a methoxy group.

An optical storage medium of the present invention comprises a photochromic material which is an aggregate containing the above-mentioned spiropyran compound as a chromophore.

In a preferred embodiment, the aggregate is an H aggregate formed from a spiropyran compound of claim 1 and one selected from the group consisting of hydrocarbons and compounds containing an ether group.

In a preferred embodiment, the aggregate is a J aggregate formed from the above-mentioned spiropyran compound, and one selected from the group consisting of aliphatic alcohols, aliphatic esters, aliphatic acids, and aliphatic amides.

Thus, the invention described herein makes possible the objectives of: (1) providing a novel photochromic material capable of forming two kinds of aggregates, each having a sharp absorption peak; and (2) providing a photochromic material comprising a spiropyran compound capable of forming a J aggregate and an H aggregate.

BRIEF DESCRIPTION OF THE DRAWING

This invention may be better understood and its numerous objects and advantages will become apparent to those skilled in the art by reference to the accompanying drawing as follows.

DESCRIPTION OF THE PREFERRED EMBODIMENTS

Figure 1:
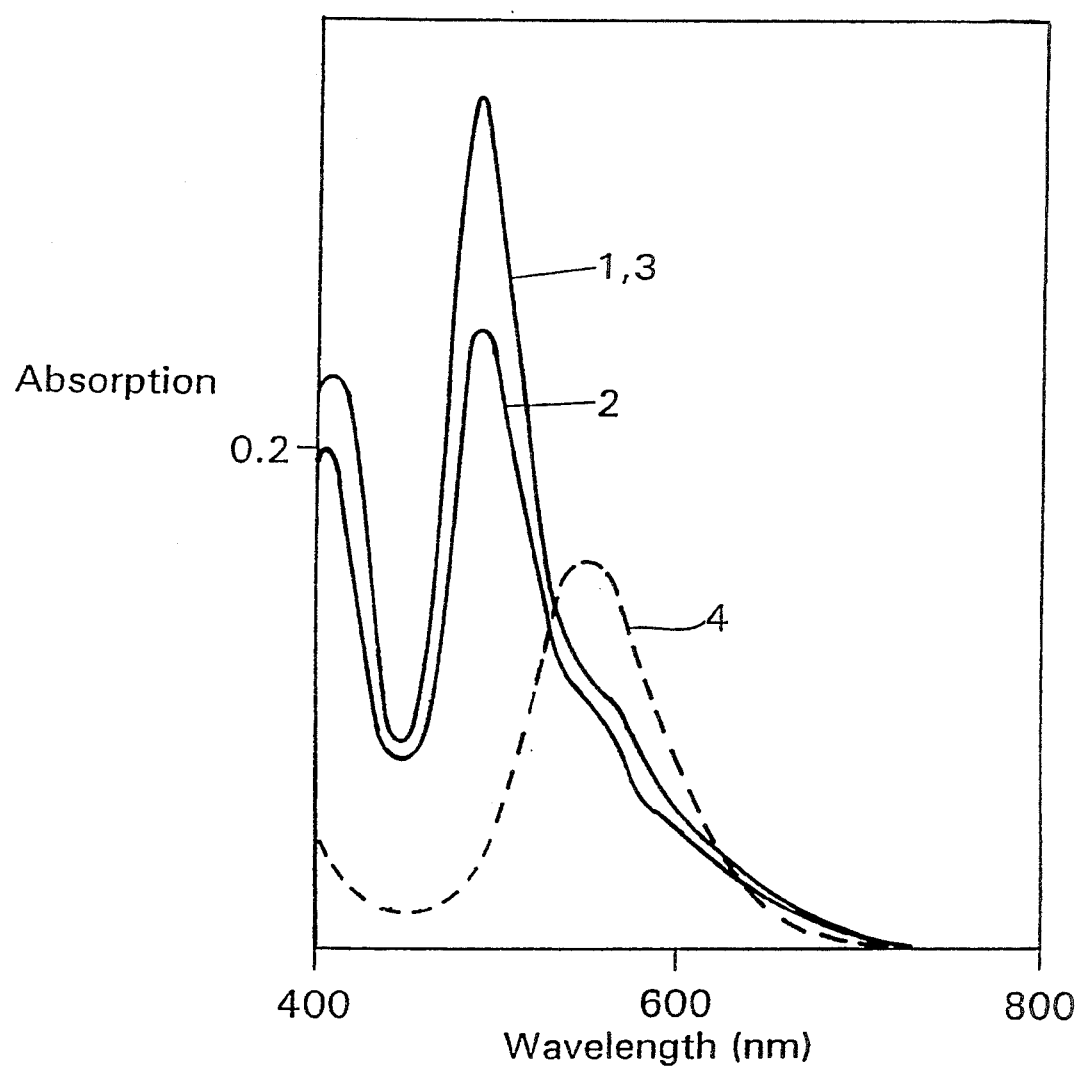
FIG. 1 is a graph showing visible absorption spectrums of (1) an initial state with a UV irradiation to a storage medium which is obtained by using a photochromic material comprising a spiropyran compound MSP1822 prepared in Example 1 of the present invention and octadecane, (2) a recording state of the storage medium recorded with a semiconductor laser device, (3) an erasing state of the storage medium erased with a UV irradiation, and (4) an initial state with a UV irradiation to a storage medium which is obtained by using a spiropyran compound MSP1822alone.

The photochromic material of the present invention comprises a spiropyran compound represented by the following general formula:

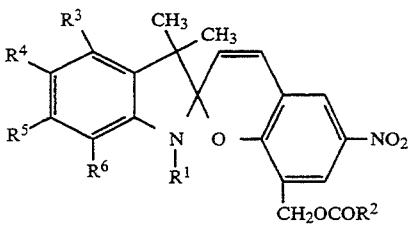

(I)

wherein $R^1$ and $R^2$ are independently alkyl groups each containing 1 to 30 carbon atoms, and $R^3$, $R^4$, $R^5$, and $R^6$ are independently selected from the group consisting of hydrogen, an amino group, an alkoxy group with 1 to 5 carbon atoms, and an alkylamino group with 1 to 5 carbon atoms with the proviso that at least one of $R^3$, $R^4$, $R^5$, and $R^6$ is an amino group, an alkoxy group or an alkylamino group.

As described above, the spiropyran compound of the present invention has an alkyl group $R^1$ at the 1' position, a nitro group at the 6 position, an alkanoyloxymethyl group ($-CH_2OCOR^2$) at the 8 position, and electron donating groups at at least one position selected from the 4' to 7' positions. The alkyl group $R^1$ at the 1' position is a straight chain alkyl group containing 1 carbon atom (i.e., $R^1$ is a methyl group) to 30 carbon atoms (i.e., $R^1$ is a triacontyl group), and the alkanoyloxymethyl group ($-CH_2OCOR^2$) at the 8 position is any one of the groups having an alkyl group $R^2$ containing 1 carbon atom (i.e., $-CH_2OCOR^2$ is an acetoxymethyl group) to 30 carbon atoms (i.e., $-CH_2OCOR^2$ is a triacontyloxymethyl group). The electron donating groups at the 4' to 7' positions are an amino group, an alkoxy group containing 1 to 5 carbon atoms, and an alkylamino group containing 1 to 5 carbon atoms; and at least one of the 4' to 7' positions is substituted by at least one of these groups. The substituted position is preferably the 5' position or 7' position.

In the above-mentioned spiropyran compound, both the alkyl group $R^1$ at the 1' position and the alkanoyloxymethyl group ($-CH_2OCOR^2$) at the 8 position are hydrophobic, and a chromophore portion (i.e., the spiropyran skeleton) is hydrophilic; thus, the spiropyran compound is amphiphilic. Thus, for example, the formation of a molecular assembly such as a micell can be promoted due to the hydrophobic interaction between the alkyl chains in the spiropyran molecule, resulting in the promotion of the formation of an aggregate. The stability of phenoxyanions, which are generated when the spiropyran is converted to a colored form by irradiation with ultraviolet rays, is improved because of the electron attractivity of the nitro group at the 6 position, and the stability of indolenium cations, which are also generated when the spiropyran is converted to a colored form, is improved because of the electron donating property of the amino group, alkoxy group, and alkylamino group of the indoline ring. Accordingly, the charge separation of cations and anions in the molecules of the colored form is promoted; as a result, the electrostatic interaction between the spiropyran molecules becomes strong, and the J or H aggregate is likely to be formed. As described above, the spiropyran compound which is a photochromic material of the present invention has an amphiphilic property and a great degree of polarization (charge separation) is performed in one molecule, so that this material is likely to form an aggregate compared with the conventional materials.

A spiropyran having an electron donating group at, at least, one of $R^6$ at the 7' position and $R^4$ at the 5' position of the indoline ring is preferred, because the electron donating group exerts great effects of the electron donating property on the nitrogen atom of the spiropyran, so that this spiropyran has the great ability of forming an aggregate.

In particular, a spiropyran having a methoxy group at the $R^4$ position has a strong electron donating property due to the methoxy group and the methoxy group gives little steric hindrance, so that this spiropyran is excellent in forming an aggregate. Optical storage media using these spiropyrans as a photochromic material are excellent in stability, even when used repeatedly.

The photochromic material of the present invention is soluble in alcohols such as methanol and ethanol; ketones such as acetone and 2-butanone; esters such as ethyl acetate and n-butyl acetate; and various other kinds of solvents such as benzene, toluene, hexane, acetonitrile, dimethylformamide (DMF), and dimethylsufoxide (DMSO).

When a spiropyran compound which is a photochromic material of the present invention is used for optical storage media, the compound is dissolved in the above-mentioned solvent to form a film; and after that the obtained film is colored by irradiation with ultraviolet rays, leading to the initialization of the entire surface. The spiropyran compound is capable of forming the H or J aggregate by itself. When the film is formed by adding a predetermined compound, the spiropyran compound is more likely to form the H or J aggregate when it becomes a colored form. For example, when low polar molecules or polymers having these low polar molecules in backbone chains or side chains thereof are added to the spiropyran compound, a stable H aggregate having a sharp absorption peak in a shorter wavelength region compared with that of the ordinarily colored form of the spiropyran can be formed. The above-mentioned low polar molecules include hydrocarbon materials such as octadecane, ether type materials such as octadecylmethylether, and aromatic type materials such as polystyrene. As the most preferred added material for forming the H aggregate, there is a hydrocarbon such as octadecane.

When polar molecules or polymers having these polar molecules in backbone chains or side chains thereof are added to the spiropyran compound, a stable J aggregate having a sharp absorption peak in a longer wavelength region compared with that of the ordinary colored form of the spiropyran can be formed. The above-mentioned polar molecules include aliphatic ester type materials such as methyl stearate; aromatic esters, carboxylic acids, amines, and amides. As the most preferred added material for forming the J aggregate, there is an aliphatic ester type material such as methyl stearate.

As described above, the photochromic material (i.e., spiropyran compound) of the present invention is capable of forming the H aggregate or the J aggregate depending on the polarity of coexisting medium. That is, either the H aggregate or the J aggregate can be formed from one kind of photochromic material. When a hydrocarbon compound or an ether type compound coexists as a medium, the photochromic material forms the H aggregate when irradiated with ultraviolet rays and then heated at a temperature in the range of about 30° C. to 40° C., normally at 35° C. When an aliphatic alcohol, aliphatic ester, or aliphatic acid coexists as a medium, the photochromic material forms the J aggregate in the same way as the above. The reason for this is considered to be as follows.

When a compound having a low polarity such as hydrocarbon coexists, the compound is present in the vicinity of the end of the alkyl chain of the spiropyran compound. As a result, the alkyl groups are positioned outside, and the chromophore portions (i.e., spiropyran skeletons) are positioned inside, the chromophore portions approaching each other, thereby forming a molecular assembly (i.e., an H aggregate). In other words, an aggregate in which the faces of the chromophore portions approach to each other is formed. When a compound having a high polarity such as aliphatic acid coexists, the polar groups in the compound are present in the vicinity of the spiropyran skeleton. As a result, the alkyl chains of the spiropyran are positioned inside, and the chromophore portions are positioned outside. In this case, the interaction between the ends of the spiropyran skeleton occurs without the interaction between the surfaces of the spiropyran skeleton, whereby an aggregate is formed. That is, an aggregate in which the spiropyran skeletons gather in a head-to-tail structure is formed. Such an aggregate is called a J aggregate. The J aggregate can be a micell in which the alkyl group is positioned inside, and the spiropyran skeleton is positioned outside.

As described above, in a photochromic compound of the present invention, the degree of polarization of the chromophore portion is high and the molecule has an amphiphilic property, so that two kinds of aggregates can be formed. Since these two aggregates have sharp absorption peaks in different wavelength regions, a multifrequency storage medium can be obtained by laminating a layer having the above-mentioned spiropyran compound and a low polar compound such as the aliphatic ester together with a layer having the above-mentioned spiropyran compound and the polar compound. For example, first, the spiropyran compound is mixed with a material capable of assisting the formation of the J aggregate to form a film on a substrate such as glass, a metal vapor deposition film, or polyester. On the obtained substrate, for example, a layer made of a polymer material such as polyvinyl alcohol, polymethyl methacrylate, polystyrene, geletin, polyvinyl chrolide, or polycarbonate is formed as a separation layer, after which the same photochromic material is mixed with a material capable of assisting the formation of an H aggregate to form a film on the separation layer. The laminated body thus obtained is initialized so as to form a J aggregate and an H aggregate in the lower layer and the upper layer, respectively. Next, the J aggregate alone is changed from a colored form to a colorless form by irradiation with light having a wavelength corresponding to an absorption maximum of the J aggregate. In contrast, the H aggregate alone is changed from a colored form to a colorless form by irradiation with light having a wavelength corresponding to an absorption maximum of the H aggregate. Thus, two kinds of information can be recorded by changing the wavelength of irradiation light at the same position. Even though the above-mentioned lamination order is changed, the same characteristics can be obtained.

Hereinafter, the present invention will be described by way of illustrating examples.

EXAMPLES

Example 1

As the spiropyran compound of the present invention, a compound shown by the formula II, is exemplified (hereinafter, the compound is referred to as "MSP1822").

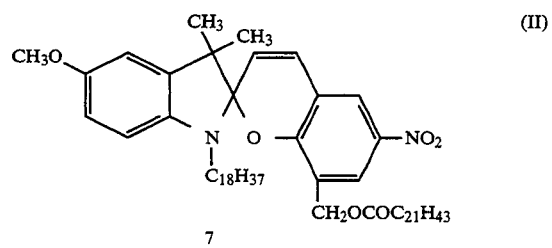

A method for the preparation of the spiropyran compound MSP1822 will be described below.

Step 1

First, 1.9 g (10 mmol) of 5-methoxy-2,3,3-trimethylindolenine 1 and 3.8 g (10 mmol) of iodooctadecane 2 were dissolved in 10 ml of chloroform; then the mixture was heated and refluxed for 40 hours. After distilling off the chloroform, the solid residue was recrystallized from 100 ml of ethanol, thereby obtaining 2.6 g (4.5 mmol, yield 45%) of 1-octadecyl-5-methoxy-2,3,3-trimethylindolenium iodide 3. This reaction can be expressed by the following chemical equation:

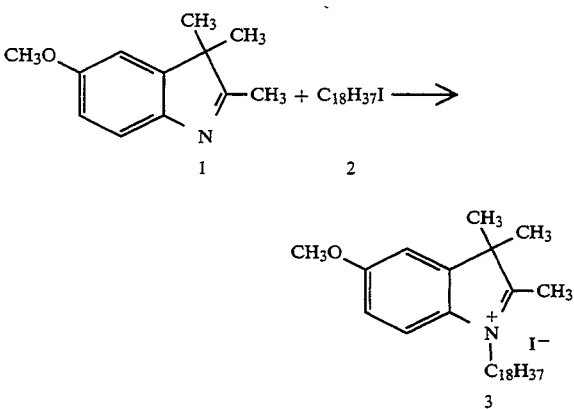

Step 2

First, 2.6 g (4.5 mmol) of 1-octadecyl-5-methoxy-2,3,3-trimethylindolenium iodine 3 obtained in Step 1 was dispersed in 50 ml of diethylether, and the mixture in turn was dispersed in 50 ml of a 4N aqueous solution of sodium hydroxide. This suspension was then stirred for 3.5 hours, after which the oily layer was extracted with diethyl ether. After being dried over sodium hydroxide for 24 hours, the diethyl ether was distilled off, thereby obtaining 1.37 g (3.1 mmol, yield 69%) of 1-octadecyl-2-methylene-3,3-dimethylindoline 4 in the form of a yellow liquid. This reaction can be expressed by the following chemical equation:

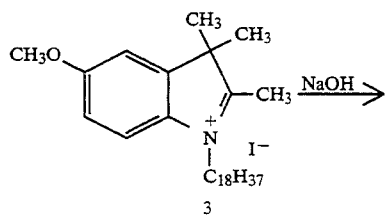

Step 3

First, 1.37 g (3.1 mmol) of 1-octadecyl -2-methylene-3,3-dimethylindoline 4 obtained in Steps 1 and 2, and 1.6 g (3.1 mmol) of 3-nitro-5-docosanoyloxymethyl-salicylaldehyde 6 were stirred in 50 ml of THF, and the THF was distilled off two hours later. The deposited precipitate was recrystallized from 100 ml of ethanol three times, thereby obtaining 1.04 g of MSP1822 (1.1 mmol, yield 28%). This reaction can be expressed by the following chemical equation:

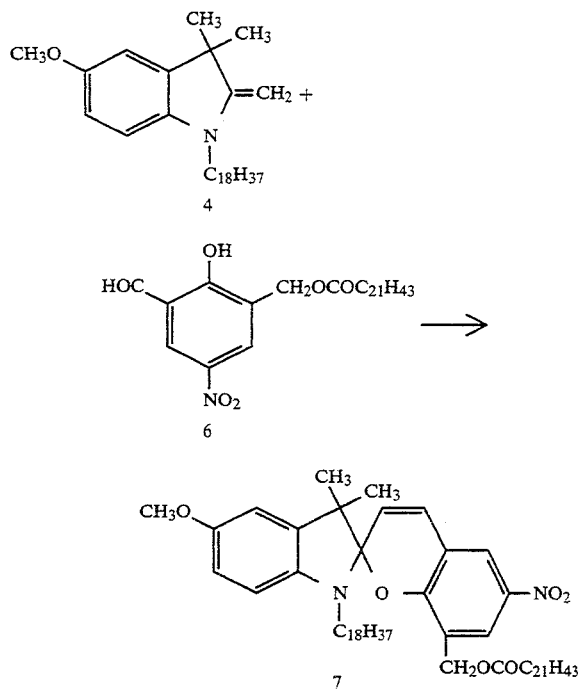

The proton NMR spectrum was measured in order to verify the structure of the product MSP1822. The result of the measurement is shown in Table 1. In Table 1, the values of chemical shift are shown in terms of ppm, and multiplicity indicated represents the form of each peak, with "s" denoting singlet, "d" doublet, "dd" double doublet, "t" triplet, and "m" multiplet. The parameter J in the Assignment column represents a coupling constant.

TABLE 1

$^1$H-NMR spectrum data of MSP1822

| Chemical shift δ (ppm) | Multi-plicity | Assignment | Number of protons |
|---|---|---|---|
| 0.92 | t | terminal methyls of long-chain alkyls J=6.8 Hz | 6 |
| 1.18 | s | 3'-methyl | 3 |
| 1.2 to 1.3 | m | methylenes of long-chain alkyls and 3'-methyl | 73 |
| 2.08 | t | methylene binding to ester carbon J=7.6 Hz | 2 |
| 3.13 | m | methylene binding to the nitorogen of the indoline skeleton | 2 |
| 3.45 | s | 5'-methoxy | 2 |
| 4.81 | s | oxymethylene | 2 |
| 5.43 | d | 3-olefin J=10.4 Hz | 1 |
| 6.12 | d | 4-olefin J=10.4 Hz | 1 |
| 6.46 | d | 7'-hydrogen J=8.4 Hz | 1 |
| 6.68 | dd | 6'-hydrogen J=8.4, 2.8 Hz | 1 |
| 6.84 | d | 4'-hydrogen J=2.8 Hz | 1 |
| 7.64 | d | 5-hydrogen J=2.4 Hz | 1 |
| 8.04 | d | 7-hydrogen J=2.4 Hz | 1 |

The spiropyran compound MSP1822 obtained in this way and octadecane were dissolved in benzene, each in a concentration of $10^{-3}$M, and the obtained solution was spin-coated onto a disk made of quartz glass at 2,000 rpm. Then, benzene was evaporated to form a thin film, thereby obtaining an optical storage medium. The thin film was colored (i.e., initialized) by irradiation with ultraviolet rays of 366 nm while heating at a temperature in the range of 30° C. to 40° C. The visible absorption spectrum of the initialized disk is shown in FIG. 1 (Curve 1). This disk could be recorded by irradiation of a laser beam having a wavelength of 490 nm, at an energy of 20 mJ/cm$^2$. The spectrum in this case, as shown by Curve 2 in FIG. 1, had a decreased absorption peak compared with Curve 1. The spot onto which the laser beam was irradiated could be returned to the initial state by irradiation with ultraviolet rays (Curve 3 in FIG. 1). No changes were observed in unrecorded storage medium and recorded storage medium after being left in a dark place at room temperature for three months or more. From the fact that an aggregate formed from this MSP1822 and octadecane had a sharp absorption maximum in a shorter wavelength region compared with that of its monomer, this aggregate was considered as an H aggregate.

Figure 2:
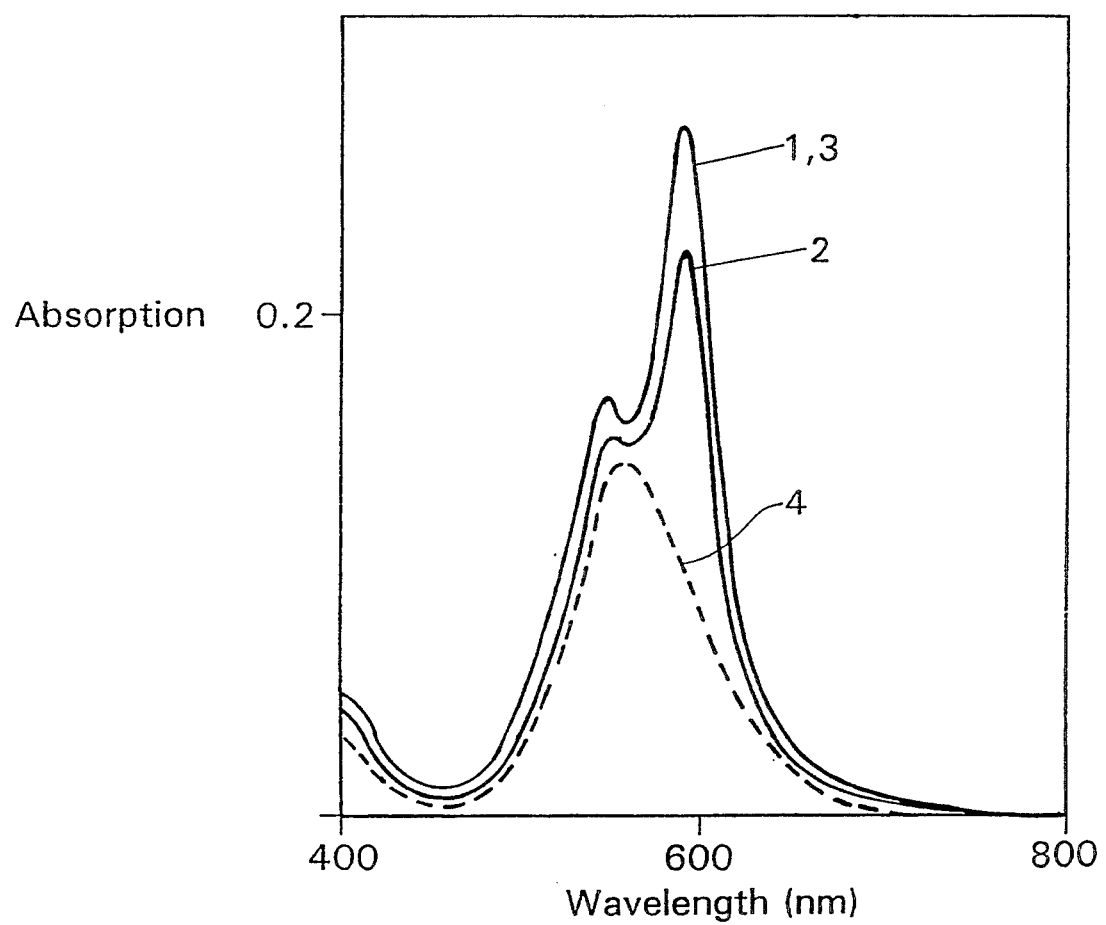
FIG. 2 is a graph showing visible absorption spectrums of (1) an initial state with a UV irradiation to a storage medium which is obtained by using a photochromic material comprising a spiropyran compound MSP1822 prepared in Example 1 of the present invention and methyl stearate, (2) a recording state of the strage medium recorded with a semiconductor laser device, (3) an erasing state of the storage medium erased with a UV irradiation, and (4) an initial state with a UV irradiation to a storage medium which is obtained by using the spiropyran compound MSP1822 alone.

On the other hand, when the compound of the present invention was made into a thin film under the following conditions, a colored form having a sharp absorption maximum in a longer wavelength region was generated. MSP1822 and methyl stearate were dissolved in benzene, each in a concentration of $10^{-3}$M, and the obtained solution was spin-coated onto a disk made of quartz glass at 2,000 rpm. Then, benzene was evaporated to form a thin film, thereby obtaining an optical storage medium. The thin film was colored (i.e., initialized) by irradiation with ultraviolet rays of 366 nm while heating at a temperature in the range of 30° C. to 40° C. to form a J aggregate. The visible absorption spectrum of the initialized disk is shown in FIG. 2 (Curve 1). This disk could be recorded by irradiation with a laser beam having a wavelength of 600 nm, at an energy of 20 mJ/cm$^2$. The spectrum in this case, as shown by Curve 2 in FIG. 2, had a decreased absorption peak compared with Curve 1 in FIG. 2. The spot onto which the laser beam was irradiated could be returned to the initial state by irradiation with ultraviolet rays (Curve 3 in FIG. 2). No changes were observed in unrecorded storage medium and recorded storage medium after being left in a dark place at room temperature for three months or more. From the fact that an aggregate formed from this MSP1822 and methyl stearate had a sharp absorption maximum in a longer wavelength region compared with that of its monomer, this aggregate was considered as a J aggregate.

As described above, a plurality of different sharp absorption peaks could be obtained from the MSP1822 by changing the material to be mixed with spiropyran compound MSP1822.

The thin film comprising MSP1822 thus obtained and octadecane, and the thin film comprising MSP1822 and methyl stearate were irradiated with ultraviolet rays and visible light alternately under the following conditions, thereby examining the reproducibility (recycle characteristics). As a result, reproducibility was observed 1,000 times and more, which was 5 times at least higher compared with that of the conventional spiropyran material.

Coloration: ultraviolet lamp (366 nm), 5 mW, 5 min.

Discoloration: wavelength 490 nm, 20 mJ/cm² (H aggregate); wavelength 600 nm, 20 mJ/cm² (J aggregate).

EXAMPLE 2

The spiropyran compound MSP1822 obtained in Example 1 and octadecane were dissolved in benzene each in a concentration of $10^{-3}$ M, and the obtained solution was spin-coated onto a disk made of quartz glass at 2,000 rpm. Then, the benzene was evaporated to form a thin film which corresponds to a first storage layer. Then, polyvinyl alcohol was dissolved in water in a concentration of $10^{-3}$ M and was spin-coated onto the thin film at 2,000 rpm, followed by evaporating water to form a separation layer. Next, MSP1822 and methyl stearate were dissolved in benzene, each in a concentration of $10^{-3}$ M and was spin-coated onto the separation layer at 2,000 rpm. Then, the benzene was evaporated to form a thin film which corresponds to a second storage layer, thereby obtaining an optical storage medium. This optical storage medium was initialized by irradiation of ultraviolet rays of 366 nm while heating at a temperature in the range of 30° C. to 40° C. By this operation, each of the spiropyran compound MSP1822 contained in the first storage layer and the second storage layer was converted into a colored form, and different types of aggregates were respectively formed in each layer. Only the first storage layer in which a J aggregate has been formed could be recorded by irradiating the optical storage medium with a laser beam having a wavelength of 600 nm at an energy of 20 mJ/cm². Only the second storage layer in which the H aggregate was formed could be recorded by irradiating the optical storage medium with a laser beam having a wavelength of 490 nm at an energy of 20 mJ/cm². As described above, a multifrequency optical strage medium could be prepared by using one kind of photochromic material.

EXAMPLE 3

As the spiropyran compound of the present invention, a compound shown by the chemical formula (III) is exemplified (hereinafter, the compound is referred to as "AASP1010").

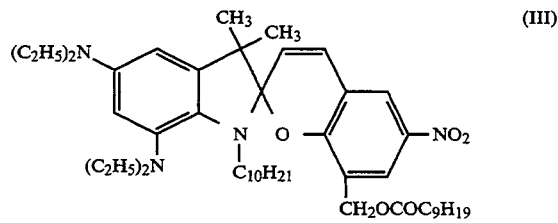

A method for the preparation of the spiropyran compound AASP1010 will be described below.

AASP1010 was prepared in the same way as in Example 1 except that Step 1 was conducted by using 5,7-bisdiethylamino-2,3,3-trimethylindolenine instead of 5-methoxy-2,3,3-trimethylindolenine 1, and iodododecane instead of iodooctadecane 2; and Step 2 was conducted by using 3-nitro-5-decanoyloxymethylsalicylaldehyde instead of 3-nitro-5-docosanoyloxymethylsalicylaldehyde.

AASP1010 also formed an H aggregate by mixing with a low polar material and formed a J aggregate by mixing with a polar material in the same way as in Example 1. The absorption wavelength of the H aggregate and the J aggregate were 485 nm and 590 nm, respectively. A multifrequency optical storage medium could be prepared by the use of these aggregates in combination. The energy level during recording and stability in a dark place at room temperature were almost the same as in Example 1.

EXAMPLE 4

The spiropyran compounds shown in Table 2 were prepared by using, as a raw material, various indolenine derivatives (substituents of which are shown in Table 2) instead of the indolenine derivative in Example 1. The respective spiropyran compounds thus obtained formed H aggregates by mixing with a low polar material and formed J aggregates by mixing with a polar material in the same way as in Example 1. A multifrequency optical storage medium could be prepared by the use of these aggregates in combination. The energy level during recording and stability in a dark place at room temperature were almost the same as in Example 1. The absorption maximum of the H aggregates and the J aggregates of the respective spiropyran compounds are shown in Table 2.

TABLE 2

| $R^1$ | $R^2$ | $R^3$ to $R^6$ | H aggregate | J aggregate |
|---|---|---|---|---|
| $CH_3$ | $C_{30}H_{61}$ | 6',7'-$NH_2$ | 480 | 595 |
| $C_2H_5$ | $C_{21}H_{43}$ | 7'-$OCH_3$ | 482 | 590 |
| $C_{10}H_{21}$ | $CH_3$ | 6'-$OCH_3$ | 486 | 592 |
| $C_{10}H_{21}$ | $C_9H_{19}$ | 5'-$(C_2H_5)_2N$ | 485 | 590 |
| $C_{18}H_{37}$ | $C_{21}H_{43}$ | 5',7'-$OCH_3$ | 490 | 600 |
| $C_{18}H_{37}$ | $C_{30}H_{61}$ | 4'-$NH_2$ | 480 | 585 |
| $C_{30}H_{61}$ | $CH_3$ | 4',5',6'-$OC_2H_5$ | 470 | 580 |

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A photochromic material comprising a spiropyran compound capable of forming a J aggregate and an H aggregate;

said spiropyran compound being selected from the group consisting of a spiropyran compound of formula I:

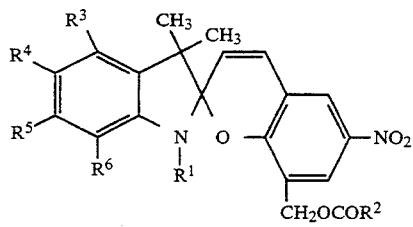

wherein $R^1$ and $R^2$ are independently alkyl groups each containing 1 to 30 carbon atoms, and $R^3$, $R^4$, $R^5$, and $R^6$ are independently selected from the group consisting of hydrogen, an amino group, an alkoxy group with 1 to 5 carbon atoms, and an alkylamino group with 1 to 5 carbon atoms with the proviso that at least one of $R^3$, $R^4$, $R^5$, and $R^6$ is an amino group, an alkoxy group or an alkylamino group.

2. A photochromic material according to claim 1, wherein at least one of $R^4$ and $R^6$ is selected from the group consisting of an amino group, an alkoxy group containing 1 to 5 carbon atoms, and an alkylamino group containing 1 to 5 carbon atoms.

3. A photochromic material according to claim 1, wherein at least one of $R^4$ and $R^6$ is a methoxy group.

4. A photochromic material according to claim 3, wherein $R^1$ is an octadecyl group, $R^2$ is a heneicosyl group, $R^3$, $R^5$ and $R^6$ are hydrogen, $R^4$ is a methoxy group.

* * * * *